United States Patent [19]
Molnar et al.

[11] Patent Number: 4,869,257
[45] Date of Patent: Sep. 26, 1989

[54] ULTRASONIC MECHANICAL SECTOR SCANNING TRANSDUCER PROBE ASSEMBLY

[75] Inventors: Arpad Molnar, Northford; Darwin P. Adams, Guilford; James Dockendorff, West Haven; Phillipp J. Quedens, Berlin; Peter J. Dutko, Durham, all of Conn.

[73] Assignee: Picker International, Inc., Cleveland, Ohio

[21] Appl. No.: 191,539

[22] Filed: May 9, 1988

Related U.S. Application Data

[62] Division of Ser. No. 740,565, Jun. 3, 1985, Pat. No. 4,773,426.

[51] Int. Cl.[4] .............................................. A61B 8/00
[52] U.S. Cl. ................................... 128/660.10; 73/633
[58] Field of Search ................ 128/660, 660.09, 660.1; 439/435–439; 73/633

[56] References Cited

U.S. PATENT DOCUMENTS

| | | | |
|---|---|---|---|
| 4,081,206 | 3/1978 | Lee | 439/457 X |
| 4,426,886 | 1/1984 | Finsterwald et al. | 73/633 |
| 4,515,017 | 5/1985 | McConaghy | 128/660.1 X |
| 4,517,985 | 5/1985 | Teslawski et al. | 128/660 |
| 4,530,362 | 7/1985 | Hetz | 128/660.1 |
| 4,649,925 | 3/1987 | Dow et al. | 128/660.1 |

FOREIGN PATENT DOCUMENTS 0024986 9/1903 United Kingdom ................ 439/456

Primary Examiner—Francis Jaworski
Attorney, Agent, or Firm—Watts, Hoffmann, Fisher & Heinke Co.

[57] ABSTRACT

An improved ultrasonic mechanical sector scanning transducer assembly is disclosed. An ultrasonic transducer is disposed for movement within a generally tubular housing. A drive element extends longitudinally within the housing and is coupled for transmitting motion to the transducer. Power means produces oscillatory rotative movement of the drive element and transducer. A diaphragm seal, comprising a resilient tubular membrane, provides a liquid tight seal between longitudinally displaced interior sections of the housing. The tubular membrane has one relatively narrow end and flares along its length to a wider opposite end. The narrow end is bonded about the drive element. The wider end is affixed about the periphery of the housing. A coaxial cable is coupled to the transducer and extends to the exterior of the housing. The cable is wrapped within a spiral groove extending about the outer surface of a spool or reel mounted for movement in unison with the transducer.

6 Claims, 2 Drawing Sheets

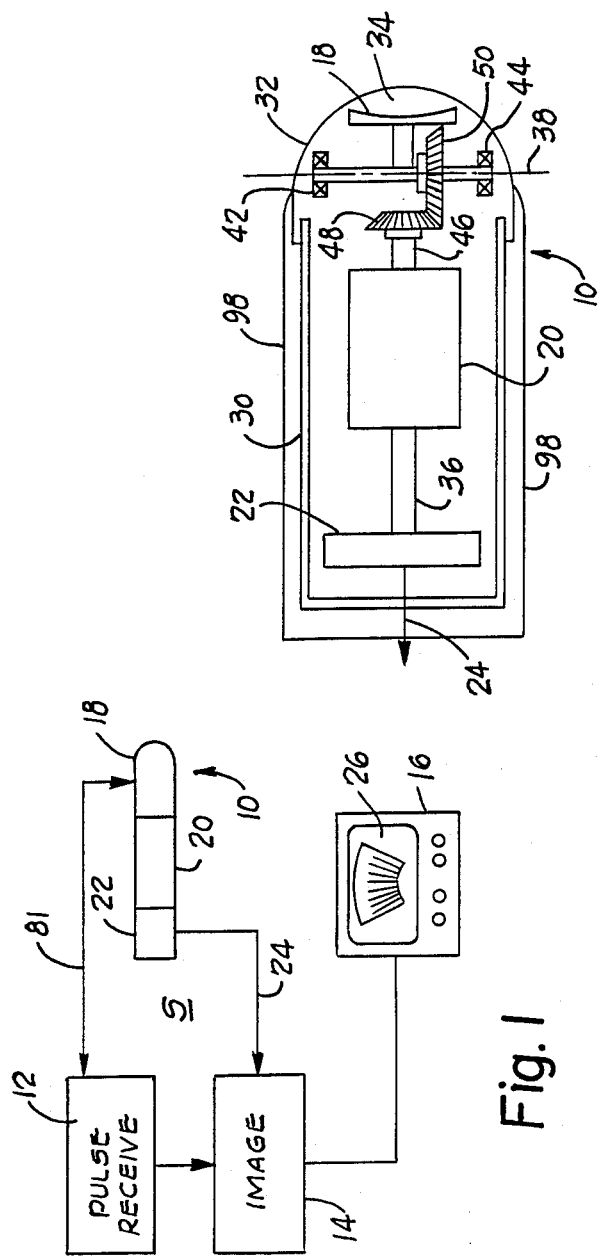

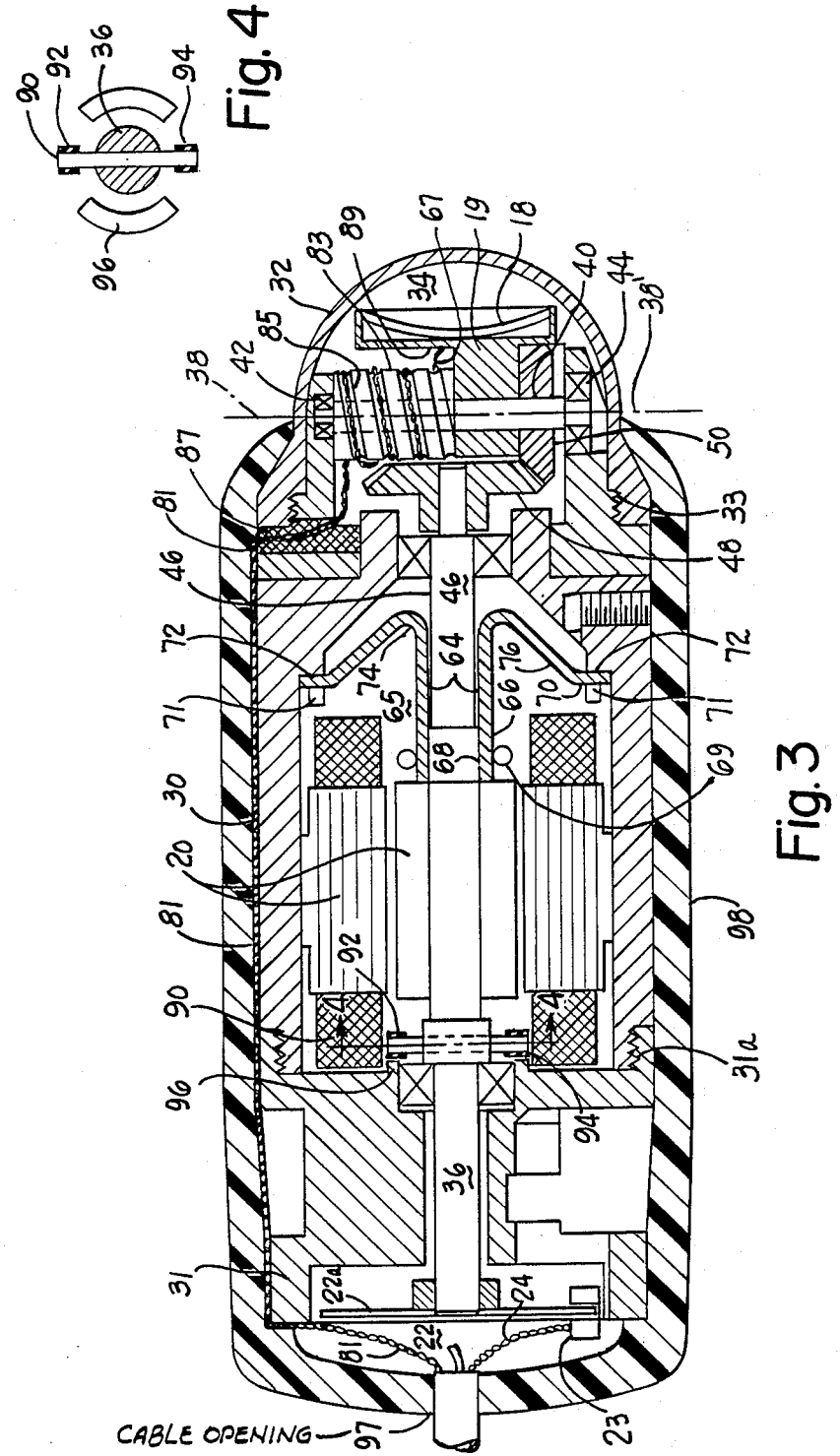

ULTRASONIC MECHANICAL SECTOR SCANNING TRANSDUCER PROBE ASSEMBLY

DESCRIPTION

This is a division of application Ser. No. 740,565 filed 6/3/85 and now U.S. Pat. No. 4,773,426.

1. Technical Field

This invention pertains to the field of ultrasonic imaging, and more particularly to improvement in ultrasonic transducer probe assemblies for use in medical diagnostic ultrasonic mechanical sector scan imaging.

2. Background Art

Ultrasonic imaging systems have long been used in the field of medical diagnostics. Such systems include an ultrasonic transducer, imaging electronics and display apparatus. The imaging electronics actuate the transducer for propagation of incident ultrasonic energy into a nearby patient's body. Within the patient's body, the ultrasonic energy causes echoes at interfaces between body tissues having different acoustical impedance characteristics. Some of these echoes are reflected back to the transducer which converts them to electrical output signals. The imaging electronics process the electrical output signals to cause the display apparatus to produce visual images representing internal structure of the patient's body.

Some ultrasonic systems are capable of imaging in real time. One type of such system employs an ultrasonic probe assembly including a movably mounted ultrasonic transducer enclosed within a chamber containing a fluid ultrasonic couplant material. In one such system, the transducer is mounted for pivotal movement about an axis, and a motor is provided to pivotally oscillate the transducer back and forth about its axis by way of a drive element or shaft coupled between the motor and the transducer. An encoder is coupled to the motor to indicate the instantaneous angular position of the transducer. The imaging circuitry senses both the ultrasonic echo representing output signals, and the encoder signal indicating transducer orientation, to produce an image appropriately corresponding to the spatial pattern of received ultrasonic echoes. The imaging circuitry takes into account both the distance between the transducer and the origin of the echoes, and the transducer angular position, which together defines the location in space of the echoes.

Examples of prior art mechanically scanned transducer ultrasonic imaging systems are set forth in the following U.S. patents, which are hereby incorporated by reference: U.S. Pat. No. 4,238,962, issued on Dec. 16, 1980, to Taenzer; U.S. Pat. No. 3,886,490, to Green.

In one example of an ultrasonic probe assembly, a stepper motor is used to power the transducer movement while simultaneously providing positional information regarding transducer orientation. The motor is coupled through a gear head comprising one bevel gear which drives another bevel gear, to which the transducer is coupled.

Another probe assembly is powered by a brushless D.C. motor. A rotary transformer is coupled to the motor for use as a position sensor. The transducer is driven by a bevel gear set, one mounted on the motor shaft, the other to the transducer.

Commonly, the ultrasonic transducer and the drive coupling structure, such as the bevel gear arrangements described above, are immersed within a probe housing in a fluid ultrasonic couplant. At least two proposals have been made for effecting a seal of the fluid couplant inside the probe. According to one proposal, the entire probe housing is sealed and its interior is completely flooded with couplant. The quality of the sealing can be very good in this instance, but all the parts within the probe housing, including the electric motor, must work under immersed conditions. This requirement limits the choice of components, and adversely affects reliability of operation.

According to another proposal, a rotary or shaft seal is provided within the housing, dividing the housing into a "wet" section and a "dry" section. The transducer and gear coupling arrangement are within the wet section with the motor and encoder apparatus located in the dry section. A drive shaft extends from the motor to the gear coupling apparatus through the rotary or shaft seal. Difficulty has been experienced, however, in effecting complete liquid-impervious sealing by this means. Small leakage of fluid from the wet section to the dry section has been substantially unavoidable. This leakage can result in undesirable wetting of the electric motor components, and/or in the appearance of air bubbles in the couplant within the wet section. The presence of these air bubbles interferes with proper transmission and sensing of ultrasonic energy, and requires the fluid chamber to be refilled whenever such bubbles appear.

Also, neither of these approaches to sealing afford optimum accommodation of changes in fluid pressure in the region of the couplant.

Ultrasonic transducer probe assemblies also include electrical leads which are coupled to the ultrasonic transducer and which extend out of the confines of the transducer probe housing to the imaging circuitry located externally of the housing. Because the transducer itself oscillates, however, it has been necessary to provide for relief of strain in the electrical leads which would arise if the leads were strung taut.

One proposed solution has been to form a service loop in the electrical lead in the vicinity of the transducer. This configuration provides adequate strain protection provided that the lead is properly bent. The skill of the assembler in properly configuring the lead, however, is very important in applying this solution. Often, an inexperienced or inadequately skilled assembler does not suitably shape the loop to provide adequate strain relief. Additionally, the service loop floats freely in the ultrasonic couplant in the vicinity of the gear drive, and is sometimes caught in the drive, causing malfunction.

It is an object of this invention to provide an acoustic transducer probe assembly having an effective and flexible internal liquid-impervious seal for isolating the wet chamber in which the transducer is located and improved means for providing strain relief in electrical leads coupled to the transducer.

DISCLOSURE OF INVENTION

The disadvantages of the prior art are reduced or eliminated by the use of an improved ultrasonic mechanical scanning transducer probe assembly including a generally tubular housing and an ultrasonic transducer disposed at least partially within the housing. A drive structure is provided, including a drive shaft longitudinally extending within the housing, a motor for oscillating the drive shaft, and apparatus for coupling the shaft to the transducer. A diaphragm seal member is provided, comprising a tubular portion of resilient material bonded in a first region about the shaft circumference. The resilient material is also affixed at another region about the periphery of interior wall structure of the tubular housing.

This diaphragm seal effects a substantially liquid-impervious seal between two sections of the housing, while still accommodating transmission of considerable oscillatory drive shaft motion through the seal member. The seal is superior to previous rotatable sealing apparatus wherein the drive shaft extends through and rotates with respect to the seal, permitting fluid leakage between the sections of the housing interior defined by the seal.

Another feature of the invention involves the diaphragm seal being partially rolled back upon itself in a convoluted configuration. In this configuration, the region of bonding with the interior wall of the housing is located between the region at which the seal member is bonded to the drive shaft, and the region of the seal member which is rolled back or coiled upon itself.

This convoluted structure affords a first portion of the seal member which is generally elongated and of a diameter only slightly larger than that of the drive shaft, and a flared portion being considerably wider and extending outwardly to the interior walls of the housing. The first, or elongated tubular portion, facilitates accommodation of the seal to drive shaft rotation over a considerable range of angular displacement, while maintaining intact the bonding of the seal member to the drive shaft, thus preventing leakage. The wider, or flared, portion affords adaptability of the seal to changes in volume and/or pressure differences between the respective sections into which the seal member divides the housing.

According to a more specific aspect of the invention, the regions in which the tubular seal member is bonded are proximate respective opposite ends of the seal member.

In a specific embodiment, the motor imparts limited oscillatory rotary motion about the axis of the drive shaft of approximately ±42° about a predetermined angular position. The seal member, constructed as described, can easily accommodate drive shaft rotary motion of this magnitude while maintaining a complete bonded seal extending between the outer periphery of the drive shaft and the inner periphery of the probe housing.

Preferably, the seal comprises a tubular membrane of elastic material, such as material containing rubber.

In accordance with a further specific feature, the probe is provided with apparatus for mounting the ultrasonic transducer for rotative motion about an axis substantially perpendicular to the axis of the housing, and the coupling apparatus includes a set of beveled gears for effecting oscillotory motion of the transducer about the perpendicular axis in response to oscillatory axial rotative motion of the drive shaft.

Another specific aspect of the invention involves the provision of an optical encoder coupled to the motor for indicating the instantaneous angular position of the drive shaft and therefore also of the transducer.

Another specific feature of the invention resides in the probe housing defining, in cooperation with the diaphragm seal, a sealed fore chamber within the housing enclosing the ultrasonic transducer and the coupling apparatus.

Preferably, a liquid ultrasonic couplant material is provided within the fore chamber.

Thus, in accordance with this embodiment, the probe housing comprises a first generally cylindrical rigid portion, and a second generally cylindrical portion having a rounded end including a portion of material suitable for propagation therethrough of ultrasonic energy, to facilitate coupling of the movable ultrasonic transducer with the surface of the subject's body via the housing.

According to another feature of the invention, the transducer is coupled to an electrical lead extending to the exterior of the housing for facilitating coupling of the transducer to the imaging circuitry. Means is provided for relief of strain in this lead, notwithstanding transducer oscillatory motion. In accordance with this embodiment, a generally cylindrical spool or reel is mounted within the housing. The spool defines a spiral groove or thread extending about its outer surface and the electrical lead is wound about the spool within the groove.

The spool is mounted fixed with respect to the transducer, and moves in unison with the transducer. As the spool moves, the electrical lead alternately loosens and tightens about the spool.

In accordance with this embodiment, means is provided to maintain tension relief in the lead, while still maintaining the lead in a generally confined region, in order to prevent any loose portions of the lead from becoming caught in the drive mechanism coupling the drive shaft to the transducer.

This invention and its advantages will be further understood by reference to the following specific description, and to the drawings, in which:

BRIEF DESCRIPTION OF THE DRAWINGS

FIG. 1 is a block diagram of a system incorporating the present invention;

FIG. 2 is a side elevational view, partly in cross-section, illustrating generally components of a portion of the system of FIG. 1;

FIG. 3 is a side elevational view, partly in cross-section, illustrating in detail the portion of the system shown in FIG. 2;

FIG. 4 is a detailed cross-sectional view of a portion of the system of FIG. 3, taken along the section A—A'.

BEST MODE FOR CARRYING OUT THE INVENTION

FIG. 1 illustrates in block form an ultrasonic mechanical sector scanning imaging system S incorporating the present invention. The system includes an ultrasonic probe 10, pulse/receiving circuitry 12, imaging circuitry 14 and display apparatus 16. The system S propagates ultrasonic energy into a subject (not shown). The system responds to ultrasonic echoes thereby generated to produce a sector image 26 corresponding to the pattern of received ultrasonic echoes and indicating internal structure and/or condition of the subject's body.

The probe 10 includes an ultrasonic transducer generally indicated at 18, a motor 20 for mechanically oscillating the transducer, and an encoder 22 for providing a substantially instantaneous indication of the azimuthal orientation of the transducer.

The pulse/receiving circuitry 12 directs electrical pulsing signals over a lead 81 (FIGS. 1 and 3) to the transducer 18, causing the transducer to propagate ultrasonic energy into the subject body. When ultrasonic echoes occur at tissue interfaces within the subject's body, some of the echoes are propagated back to the transducer. In response to the echoes, the transducer produces electrical output signals which are detected via the lead 81 by the pulse/receiving circuitry 12.

The pulse/receive circuitry 12 transmits the echo indicating transducer output signals to the imaging circuitry 14. The imaging circuitry 14 also receives a signal over a lead 24 from the encoder 22 indicating substantially the instantaneous orientation of the transducer.

The imaging circuitry 14 processes the detected echo indicating signals and the orientation indicating signal from the encoder to produce, on the display apparatus 16, which comprises a CRT display set, a sector image 26 describing internal subject body structure.

FIG. 2 illustrates an in-line mechanical sector scanning probe constructed in accordance with the present invention. The probe includes a housing comprising a first portion 30 made of a generally rigid material, such as durable plastic, in a cylindrical configuration closed at the left hand end as viewed in FIG. 2. The housing also includes a sound window portion 32 having a generally hemispherically rounded configuration with its rounded end at the right, as viewed in FIG. 2. The second sound window section 32 is made of a material which facilitates the passage of ultrasonic energy between the transducer and the exterior of the housing. In use, the portion 32 of the housing is held against the subject's body in order to couple ultrasonic energy from the probe with the body.

The interior of the probe 10 in the vicinity of the transducer 18, indicated at reference character 34, is filled with a liquid acoustic couplant material.

The motor 20 comprises a brushless D.C. motor having very low inertia. The motor 20 is operated by known servo power circuitry (not shown) in a limited rotation mode. Angular displacement of the motor is approximately ±42° with respect to a predetermined center position.

The encoder 22 is an optical encoder coupled rigidly to the motor 20 by a shaft 36. It is a three channel encoder preferably having two data channels of 512 cycles per channel, and an index channel.

The transducer 18 is pivotally mounted for rotational movement about an axis 38 extending upwardly and downwardly within the plane of the paper of FIG. 2. More specifically, the transducer 18 is mounted to a shaft 40 which is journalled in bearings 42, 44 for axial movement about the axis 38, which is substantially perpendicular to the axis of the housing portion 30.

The transducer is driven by means including a drive shaft 46 of the motor 20, and is coupled to the drive shaft by way of a pair of beveled gears 48, 50. The bevel gear 48 is mounted axially on the shaft 46, the bevel gear 50 being mounted on the transducer shaft 40. The gear ratio between the gears 48, 50 is approximately 1:1.33.

FIG. 3 illustrates in detail a probe assembly embodying the present invention and corresponding to that shown in FIG. 2. The probe assembly includes a housing including the first cylindrical portion 30 and the second rounded sound window portion 32 as described in connection with FIG. 2. The motor 20 is coupled by way of the shaft 36 to the optical encoder 22 including the disk 22a and an optical reading device 23. An output over the lead 24 produces a signal indicating substantially the instantaneous rotational position of the motor 20, which is directed to the imaging circuitry 14 as described in connection with FIG. 1. A closure portion 31 encloses the shaft 36 and closes off the left hand end of the housing portion 30.

The housing portions 30, 31 are coupled by three screws (not shown) at the region 31a for easy disassembly and service. Alternately, a threaded coupling could be used.

The sound window is mounted to the housing portion 30 by threads 33. Alternately, a screw clamp structure can be used.

The transducer 18 is rigidly mounted by a coupling element 19 to the shaft 40 having a vertical axis 38, 38' as shown in FIG. 3, substantially perpendicular to the axis of the housing. The shaft 40 is journalled about the bearings 42, 44 for rotation about its axis.

The drive shaft 46 extends from the motor 20 to a location proximate the shaft 40 and is approximately co-axial with the housing portion 30. FIG. 3 shows the bevel gears 48, 50 mounted to the shafts 40, 46 to effect rotation of the shaft 40 and the transducer 18 in response to axial rotation of the shaft 46 as driven by the motor 20.

The motor 20 is driven by servo power circuitry (not shown) to effect oscillatory axial rotation of the shaft 46 approximately 42° in both directions from a predetermined central angular displacement of the shaft 46.

The probe is provided with a diaphragm seal member 64 for dividing the interior of the housing 30 and sound window 32 into a "wet" fore chamber portion 34 containing the acoustic couplant and a "dry" chamber 65, in which the motor is located. The seal member 64 must be capable of accommodating the extension therethrough of the motor drive shaft 46, and provide an effective liquid tight seal notwithstanding the very considerable oscillatory axial rotation of the shaft 46. The seal must also be capable of providing for expansion and contraction of the wet or fore chamber in response to changes in liquid temperature of the acoustic couplant within the fore chamber.

The diaphragm seal 64, shown in cross-section in FIG. 3, comprises a tubular portion of resilient membrane material, preferably E-RTV silicone rubber, made by Dow-Corning. The seal member 64 includes a relatively narrow end 66, and flares along its length to a relatively wider end 70. In the region 68 proximate its narrower end, the seal member 64 is bonded, by means of 732 RTV sealant, made by Dow-Corning, and by an O-ring 69, to the outer circumference of the drive shaft 46. Proximate the outer, or wider end 70, the seal member 64 is affixed, by clamp structure 71, at a region 72 to the periphery of interior wall structure of the housing portion 30. In this way, the seal member 64 provides a flexible, but substantially liquid-impervious, seal between the fore chamber 34 and the dry chamber 65.

Alternately, the housing 30 can be split in the region 72, the seal member inserted between the split portions, and the housing resealed together as by threaded coupling, to clamp the outer end of the seal member in place.

The diaphragm seal 64, along a substantial portion of its length adjacent its narrower end 66, as shown in FIG. 3, has a relatively constant diameter, which is only slightly larger than the diameter of the drive shaft 46. This tubular seal portion, having a relatively constant diameter, provides the required flexibility for facilitating a substantial oscillatory rotary motion of the drive shaft 46 about its axis, without generating undue forces which would tend to separate the bonded portion 68 from the shaft 46.

Moreover, this tubular configuration of the seal facilitates the seal twisting back and forth in response to drive shaft rotary motion without the material of the seal buckling. Tests have indicated that, by avoiding buckling of the seal material during motion, a seal can withstand over one hundred million rotary cycles without failure or significant wear.

Buckling of the said material would greatly accelerate seal wear, due to stress concentrations in the seal material in the region of buckling, and due to consequent rubbing of the seal on itself and on the drive shaft.

Buckling would also cause undesirable variations in torque required to rotatably oscillate the shaft about its axis.

The seal 64, in cross-section, as shown in FIG. 3, defines a convoluted configuration. The seal member is rolled back upon itself in a curved region 74. The bonded region 72 adjacent its wider end 70 is located, longitudinally with respect to the housing, intermediate the rolled back portion 74 and the bonded region 68 adjacent the narrower end 66 of the seal.

This convoluted configuration defines a flange portion 76 of the seal 64 extending generally outwardly from near the outer periphery of the drive shaft 46 to the interior of the wall structure of the housing portion 30. The flange portion 76 provides for expansion and contraction of the volume of the fore chamber in accordance with changing fluid temperature within the fore chamber.

Thus, the particular configuration of the seal member 64 provides for a facilitation of rotary movement of the shaft 46 extending therethrough, and for accommodation of changing fluid temperatures within the fore chamber, all without the exertion of strain sufficient to separate the regions 68, 72 from their adjacent structure.

Another aspect of this invention concerns the manner in which conductive electrical coupling is made with the transducer 18. As shown in FIG. 3, a conductive lead 81, is attached to the transducer 18. The lead 81, which preferably comprises a co-axial cable, delivers pulser signals to the transducer 18 for causing the transducer to propagate ultrasonic energy into the subject. The lead 81 also carries transducer output signals from the transducer, representing detected ultrasonic echoes reaching the transducer, back to the pulse/receiving circuitry 12, as shown in FIG. 1.

Structure is provided for affirmatively maintaining the portion of the cable 81 within a confined region of the fore chamber, in a relatively fixed location, while still providing for cable strain relief in the form of slack, to prevent undue strain from being imposed on the cable during transducer oscillatory motion.

The strain relief means comprises a spool or reel 83 which is rigidly mounted co-axially with respect to the shaft 40, and thus moves in unison with transducer oscillations. The spool 83 is preferably made from a plastic material having a low coefficient of friction, such as that known by the trademark Delrin. The outer surface of the spool defines a generally spiral thread or groove 85. The spiral groove 85 defines a rounded bottom, when viewed in cross-section as in FIG. 3.

In use, the co-axial cable 81 is wound for about three turns about the spool 83 within the groove 85, along the portion of the co-axial cable 81 between its point of exit 87 from the housing portion 32 and its location 67 of coupling to the transducer 18.

The cable is wound so that, when the spool rotates +65° from its center position, the cable is just taut. This assures that the cable remains loose during the normal spool rotation. The grooves on the spool serve to separate the cable turns. Rubbing of the cable on itself could result in premature cable failure.

As the transducer 18 is oscillated by axial rotative movement of the shaft 40, the spool 83 also rotates in unison. The loosely wound cable 81 alternately loosens and tightens in the groove defined in the spool 83. By use of the grooved spool 83 as a strain relief means, the cable is maintained in generally a non-time varying configuration within the chamber 34, while at the same time being allowed to alternately loosen and tighten, avoiding undue strain on the cable and its coupling to the transducer 18.

A stop pin 90 (see FIGS. 3 and 4) extends diametrically through the shaft 36. In case of servo drive failure of the motor 20, the transducer, spool, co-axial cable, bevel gear assembly and diaphragm seal 64 are thereby protected from damage which would result from over-rotation and from undue abruptness of motion.

Two rubber sleeves 92, 94 are placed to cover opposite ends of the pin 90. Structure 96 of the housing end cover portion 31 defines a stop for the pin at ±42° shaft rotation to prevent the overtravel.

The entire probe, with the exception of the sound window and a cable opening 97 at the opposite end, is enclosed by a protective plastic cover or sheath 98 (see FIG. 3). The sheath 98 additionally provides insulation and enhances the appearance of the instrument.

The cable 81 extends under the sheath 98 along the length of the probe housing to the opening 97, where it exits the probe, along with the lead 24 from the encoder 22.

It is to be understood that the description herein is intended to be illustrative, rather than exhaustive, of the invention. Those of ordinary skill in the relevant art may be able to make certain additions, deletions and/or modifications with respect to the disclosed embodiments without departing from the spirit or the scope of the invention, as defined in the appended claims.

We claim:

1. An ultrasonic probe assembly comprising:
 (a) a housing;
 (b) an ultrasonic transducer movably mounted for pivotal motion within said housing;
 (c) a generally cylindrical spool defining a spiral groove on its outer surface and mounted within said housing for movement in unison with said transducer within said housing;
 (d) an electrical lead coupled to said transducer and extending to a location external to said transducer to for facilitating coupling of said transducer to external circuitry.

2. The assembly of claim 1, wherein:
 said electrical lead comprises a coaxial cable.

3. The assembly of claim 1, wherein:
 said spool comprises a material designated by the trademark Delrin.

4. The assembly of claim 1, wherein:
 said groove defines a generally rounded bottom configuration.

5. The assembly of claim 1, further comprising:
 (a) said housing being generally cylindrical in configuration, and (b) said transducer and said spool being mounted for pivotal motion about an axis substantially perpendicular to the axis of said housing.

6. An ultrasonic probe assembly comprising:
(a) a housing;
(b) an ultrasonic transducer mounted for rotational motion within said housing;
(c) a generally cylindrical grooved spool mounted within said housing for rotational movement in unison with said rotational movement of said transducer, and
(d) an electrical lead connected to said transducer and extending to the exterior of said housing, said electrical lead being wrapped about the circumferential surface of said spool.

* * * * *